US00PP32480P2

(12) United States Plant Patent
Van Swieten

(10) Patent No.: US PP32,480 P2
(45) Date of Patent: Nov. 17, 2020

(54) ***PHALAENOPSIS* ORCHID PLANT NAMED 'PHALGREKK'**

(50) Latin Name: ***Phalaenopsis* hybrid**
Varietal Denomination: PHALGREKK

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/873,358

(22) Filed: Mar. 26, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named, 'PHALGREKK', QZ PBR 53276, published Jun. 15, 2018.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALGREKK', particularly characterized by white flowers with yellow-white lips, many branches, a compact plant, and is propagated by meristem tissue culture, is disclosed.

3 Drawing Sheets

Genus and species: *Phalaenopsis* hybrid.
Variety denomination: 'PHALGREKK'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGREKK'.

The new *Phalaenopsis* plant is a product of a planned breeding program conducted by the inventor in Bleiswijk, the Netherlands. The objective of this breeding program was to create a new *Phalaenopsis* plant with many branches and white flowers with yellow-white lips, suitable for potted plant production.

The new *Phalaenopsis* plant 'PHALGREKK' is a result of cross-pollination made by the inventor in December 2009 in Bleiswijk, the Netherlands, of the proprietary female, or seed parent, *Phalaenopsis* hybrid '01-3324' (unpatented) with the proprietary male, or pollen parent, *Phalaenopsis* hybrid '22444-010' (unpatented).

The new *Phalaenopsis* was selected by the inventor as a single plant within the progeny of the stated cross-pollination in a controlled greenhouse in Bleiswijk, the Netherlands, in November 2012. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 26, 2018, by Applicant who obtained the subject matter disclosed directly from the inventor. 'PHALGREKK' has not been made publicly available or sold anywhere in the world prior to the effective filing date of this application with the exception of sales or disclosures made one year or less before the effective filing date of this claimed invention by Applicant who obtained 'PHALGREKK' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGREKK' as a new and distinct variety of *Phalaenopsis* plant:

1) White flowers with yellow-white lips;
2) Plant has many branches; and
3) Compact plant.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in February 2020. Colors in the photographs may differ from the color values cited in the detailed botanical description, which accurately describe the actual colors of the new variety.

DESCRIPTION OF THE NEW VARIETY

Figure 1:
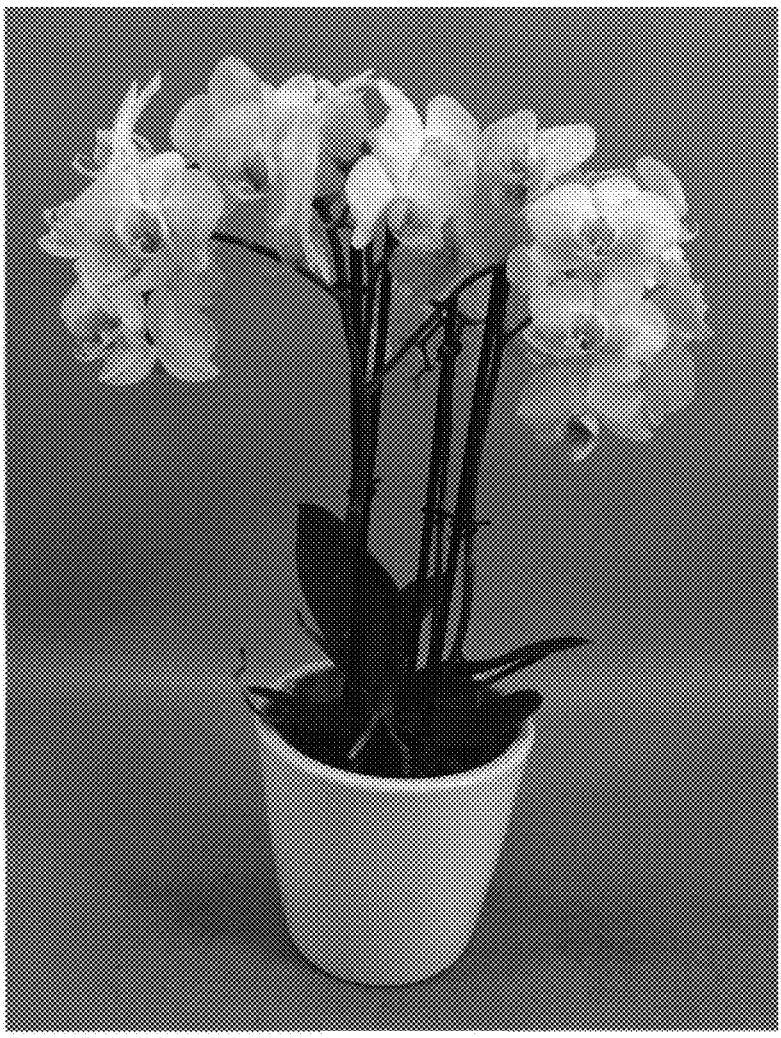
FIG. 1 shows the overall plant habit, including blooms and foliage of 'PHALGREKK'.
Figure 2:
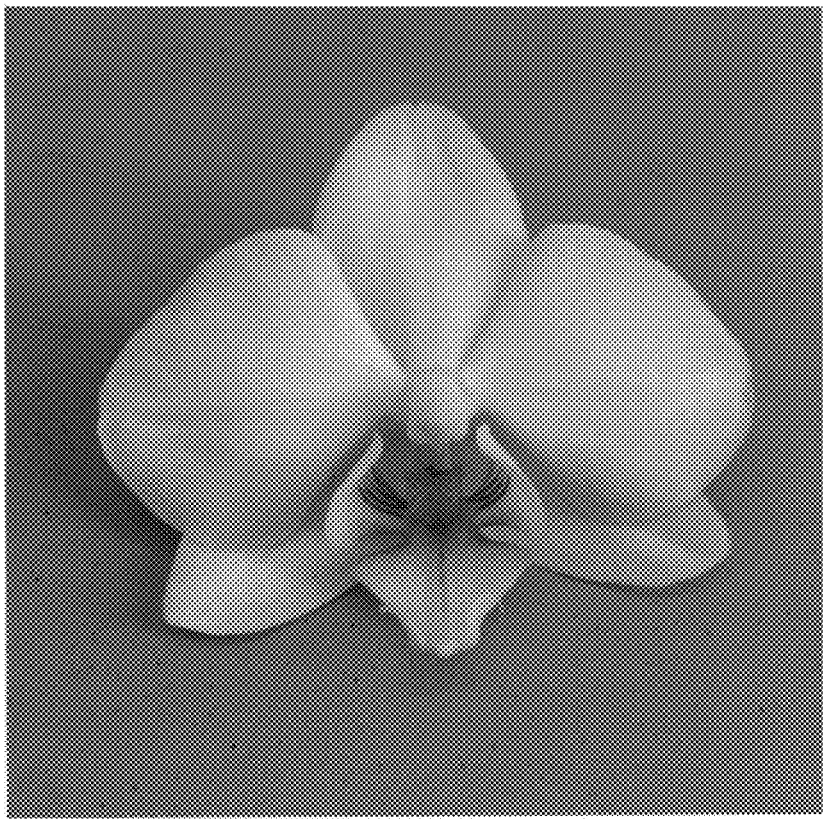
FIG. 2 shows a close-up of a flower of 'PHALGREKK'.
Figure 3:
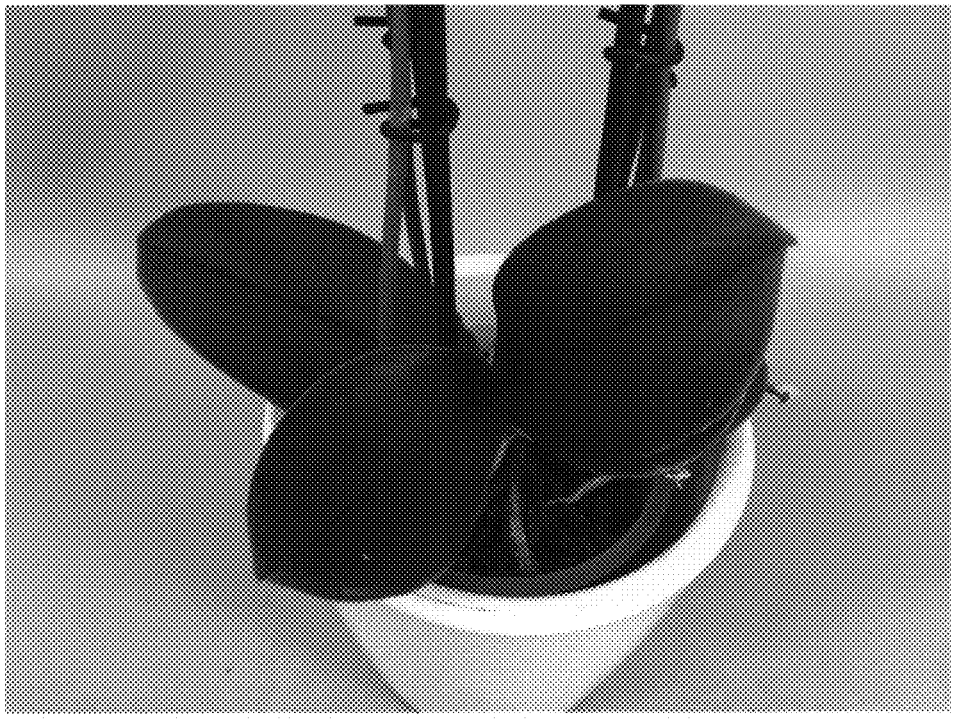
FIG. 3 shows an overhead view of the leaves of 'PHALGREKK'.

The following detailed description sets forth the distinctive characteristics of 'PHALGREKK'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGREKK'.

Parentage:

*Female parent*.—*Phalaenopsis* cultivar '01-3324' (unpatented).

*Male parent*.—*Phalaenopsis* cultivar '22444-010' (unpatented).

Propagation:

*Type*.—Meristem tissue culture.

Roots:

*Root description*.—Greyed-green (something between RHS 190B and 190C) colored roots with branching lateral roots having yellow-green (RHS 146D) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height (from soil level to top of inflorescence)*.—Approximately 37.0 cm to 42.0 cm.

*Width (measured from leaf tips)*.—About 19.0 cm to 21.0 cm.

*Vigor*.—Strong.

Leaves:

*Mature leaves*.—Quantity per plant: 7 to 8 leaves are produced before flowering. Length (fully expanded): 10.0 cm to 12.0 cm. Width: 5.0 cm to 6.0 cm. Position of the broadest part of the leaf: At the middle. Shape: Oblong. Base shape: Slightly to moderately elongated. Apex: Unequal obtuse. Leaf blade angle with the petiole (measured from the horizontal position): Between 20 degrees and 45 degrees. Leaf margin: Entire. Color: Upper surface: RHS 147A. Lower surface: RHS 147B. Texture (both upper and lower surfaces): Smooth. Thickness: 2.6 mm to 2.9 mm. Variegation: Absent. Venation: Pattern: Parallel. Color of the midvein: Upper surface: RHS 147A. Lower surface: RHS 146A.

Peduncle:

*Quantity per plant*.—2 to 5.

*Number of flowers per peduncle*.—11 to 16.

*Length*.—37.0 cm to 42.0 cm.

*Diameter*.—3.0 mm to 5.0 mm.

*Strength*.—Strong.

*Aspect*.—Upright to slightly pendent.

*Texture*.—Smooth.

*Color*.—Yellow-green (RHS 144A).

*Internode length*.—4.0 cm to 5.0 cm.

Inflorescence description:

*Appearance*.—Upright to slightly pendent, panicle inflorescence with bilaterally symmetrical flowers that open in succession beginning with the lowermost flower.

*Number of inflorescences*.—2 to 5.

*Inflorescence size*.—Height (from base to tip): 160.0 mm to 220.0 mm.

*Flowering time*.—First flowers can be expected 10 to 11 months after planting in a 12-cm pot.

*Flower*.—Height: 53.0 mm to 58.0 mm. Diameter: 60.0 mm to 65.0 mm. Depth of lip: 16.0 mm to 18.0 mm.

*Flower longevity*.—On the plant: 8 to 11 weeks.

*Flower shape*.—Flat.

*Fragrance*.—Absent.

*Flower bud*.—Average size: Medium to large. Length: 20.0 mm to 22.0 mm. Width: 17.0 mm to 19.0 mm. Shape: Egg shaped. Color: Light yellow-green (RHS 145C and 150C).

*Petals*.—Arrangement: Open/free. Shape: Semi-circular. Apex: Obtuse asymmetric. Margin: Entire. Length (from base to tip): 28.0 mm to 30.0 mm. Width: 31.0 min to 33.0 mm. Position of the broadest part of the petal: Toward the base. Color (when fully opened): Upper surface: Basic color: White (RHS NN155C). Over color: Absent. Lower surface: Basic color: White (RHS NN155C). Over color: Absent. Number of spots and stripes on the petals (upper surface): None. Color of spots and stripes on the petals (upper surface): None. Density of netting of the petals (upper surface): None. Color of the netting (upper surface): None.

*Dorsal sepal*.—Shape: Elliptic. Apex: Rounded to slightly emarginated symmetric. Margin: Entire. Length (from base to tip): 31.0 mm to 33.0 mm. Width: 22.0 mm to 24.0 mm. Position of the broadest part of the dorsal sepals: At the middle. Color (when fully opened): Upper surface: Basic color: White (RHS NN155C). Over color: Absent. Lower surface: Basic color: White (RHS NN155C). Over color: Absent. Number of spots and stripes on the dorsal sepals (upper surface): None. Color of spots and stripes on the dorsal sepals (upper surface): None. Density of netting of the dorsal sepals (upper surface): None. Color of the netting: None.

*Lateral sepals*.—Shape: Ovate. Apex: Acute symmetric. Margin: Entire. Length (from base to tip): 32.0 mm to 34.0 mm. Width: 20.0 mm to 22.0 mm. Position of the broadest part of the lateral sepals: Toward the base. Color (when fully opened): Upper surface: Basic color: White (RHS NN155C). Over color: Hint of light reddish-purple (RHS N78D) at the base. Lower surface: Basic color: White (RHS NN155C). Over color: Light yellow-green (RHS 145D) at the base. Number of spots and stripes on the lateral sepals (upper surface): None. Color of spots and stripes on the lateral sepals (upper surface): None. Density of netting of the lateral sepals (upper surface): None. Color of the netting (upper surface): None.

*Labellum* (*lip*).—Whiskers: Present. Length of whiskers: 9.0 mm to 11.0 mm. Color of whiskers: White (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 15.0 mm to 17.0 mm. Width: 12.0 mm to 14.0 mm. Color: Upper surface: Yellow margin (RHS 7A) on one side at the base with reddish-purple stripes (RHS 184C) and red (RHS 182B); white (RHS NN155C) toward the other margin. Lower surface: Yellow (RHS 7B) on one side; white (RHS NN155C) toward the other side. Number of spots and stripes on the lateral lobe: Few stripes. Color of spots and stripes on the lateral lobe: Reddish-purple (RHS 184C) and red (RHS 182B). Density of netting of the lateral lobe: None. Color of the netting: None.

*Apical lobe*.—Shape: Triangular. Margin: Entire. Length: 17.0 mm to 19.0 mm. Width: 17.0 mm to 19.0 mm. Color: Upper surface: Brownish-orange margin (RHS 166C) at the base; greenish-yellow (RHS 3A) at the base; white (RHS NN155C) toward whiskers. Lower surface: Brownish-orange margin (RHS 166C) at the base; greenish-yellow (RHS3B) at the base; white (RHS NN155C) toward whiskers. Number of spots and stripes on the apical lobe: One stripe in the middle. Color of spots and stripes on the apical lobe: RHS 166C. Density of netting of the apical lobe: None. Color of the netting: None.

*Callus*.—Average size: Small to medium. Height: 0.6 cm to 0.7 cm. Length: 0.4 cm to 0.5 cm. Width: 0.3 cm to 0.4 cm. Color: Yellow (RHS 13B) with dark reddish-orange spots (RHS 176A).

Reproductive organs:

*Column*.—Length: 7.0 mm to 9.0 mm. Diameter: 4.0 mm to 5.0 mm. Color: White (RHS NN155C).

*Pollinia*.—Quantity: 2. Diameter: 0.7 mm to 0.9 mm. Color: Yellow-orange (RHS 23A).

*Ovary*.—Length: 8.0 mm to 10.0 mm. Diameter: 2.1 mm to 2.3 mm.

*Pedicel*.—Length: 25.0 mm to 27.0 mm. Diameter: 2.4 mm to 2.6 mm. Texture: Smooth. Color: Yellow-green (RHS 145A) at the base; light yellow-green (RHS 145C) with a hint of very light purple (RHS 76B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent plant of 'PHALGREKK', cultivar '01-3324' (unpatented), is no longer in existence, therefore a meaningful comparison cannot be made.

'PHALGREKK' differs from male parent plant '22444-010' (unpatented) in that 'PHALGREKK' has white whiskers and small to medium calluses, whereas '22444-010' has very light yellow whiskers and large calluses. Additionally, 'PHALGREKK' has smaller flowers and a smaller lip depth than '22444-010'.

'PHALGREKK' is most similar to the commercial *Phalaenopsis* plants named 'PHALDUEL' (U.S. Plant Pat. No. 28,256) and 'PHALDRIDOP' (U.S. Plant Pat. No. 28,980). 'PHALGREKK' differs from the commercial variety 'PHALDUEL' in that 'PHALGREKK' has obtuse petal apexes and obtuse leaf apexes, whereas 'PHALDUEL' has rounded petal apexes and acute leaf apexes. Additionally, 'PHALGREKK' has wider dorsal sepals than 'PHALDUEL'.

'PHALGREKK' differs from the commercial variety 'PHALDRIDOP' in that 'PHALGREKK' has obtuse leaf apexes and a very small area of over color on the lateral sepals, whereas 'PHALDRIDOP' has rounded leaf apexes and no over color on the lateral sepals. Additionally, 'PHALGREKK' has wider dorsal sepals and narrower leaves than 'PHALDRIDOP'.

I claim:

1. A new and distinct variety of *Phalaenopsis* plant named 'PHALGREKK', substantially as described and illustrated herein.

* * * * *